United States Patent
Yukawa et al.

[11] Patent Number: 5,966,458
[45] Date of Patent: Oct. 12, 1999

[54] DISPLAY SCREEN INSPECTION METHOD

[75] Inventors: Noriaki Yukawa, Nara-ken; Shoichi Ishii, Ibaraki; Hideshi Ueda, Yao, all of Japan

[73] Assignee: Matsushita Electric Industrial Co., Ltd., Osaka-fu, Japan

[21] Appl. No.: 08/881,799

[22] Filed: Jun. 24, 1997

[30] Foreign Application Priority Data

Jun. 28, 1996 [JP] Japan ................................. 8-169782

[51] Int. Cl.$^6$ ................................................. G06K 9/00
[52] U.S. Cl. ........................ 382/141; 382/149; 345/904; 348/92
[58] Field of Search ................................. 382/141, 144, 382/149, 151–152; 345/904, 214, 87, 117; 324/770; 348/86, 92, 125, 129, 126, 184, 189

[56] References Cited

U.S. PATENT DOCUMENTS

| | | | |
|---|---|---|---|
| 5,204,617 | 4/1993 | Kumagai | 345/904 |
| 5,293,178 | 3/1994 | Kobayashi | 345/904 |
| 5,504,504 | 4/1996 | Markandey et al. | 345/214 |
| 5,686,959 | 11/1997 | Hayashi et al. | 382/149 |
| 5,717,780 | 2/1998 | Mitsumune et al. | 382/149 |
| 5,764,209 | 6/1998 | Hawthorne et al. | 345/904 |
| 5,825,196 | 10/1998 | Irie et al. | 324/770 |

*Primary Examiner*—Leo H. Boudreau
*Assistant Examiner*—Bhavesh Mehta
*Attorney, Agent, or Firm*—Wenderoth, Lind & Ponack, L.L.P.

[57] ABSTRACT

A display screen inspection method according to the present invention takes a display screen of a display device as an inspection subject and makes decisions on defects of the display screen. The method includes performing a separation between display operating portions and display non-operating portions of the inspection subject present in a gray image from image data of individual pixels of the gray image obtained by picking up an image of the inspection subject, selectively extracting image data of only proper display operating portions and compressing the image data to be inspected for defects, and inspecting the selectively extracted image data for any defects.

9 Claims, 5 Drawing Sheets

DISPLAY SCREEN INSPECTION METHOD

BACKGROUND OF THE INVENTION

The present invention relates to a method for inspecting a display screen. More specifically, the invention relates to a display screen inspection method for automatically deciding the conformity of inspection results in the production line with respect to inspections for point defects and the like on display devices used in electronic equipment and other fields, such as liquid crystal panels, shadow masks, CRT panels, and plasma displays.

As a method for reading the screen displayed on a display device, there has been provided, as a primary method, one using two-dimensional CCD area sensors.

Generally, pixels arrayed in columns and rows of two-dimensional sensors, and pixels arrayed in columns and rows of a display device are associated with each other (hereinafter, unless otherwise specified, pixels of the display device will be referred to as "display pixels", and pixels of the sensors will be referred to as "sensor pixels"), where the pixel arrangement is such that a plurality of sensor pixels are associated with one display pixel.

This is explained by taking a case of a display device of a liquid crystal panel consisting of 640×400 pixels as an example. A liquid crystal panel includes display operating portions and display non-operating portions of the pixels. Point defects in the dynamic operating inspection for these display operating portions can be classified into dark dots, which are a group of display pixels that will not operate for display in the displaying state of the liquid crystal panel although they are originally intended to be a display operating portion, and bright dots, which are a group of display pixels that will operate for display in the non-displaying state although they are originally intended to be a display non-operating portion. For example, in an automatic inspection for this, when three sensor pixels are assigned to one display pixel, approximately 2000 pixels are required in the row direction.

As an example of the conventional method, there has been adopted a method in which the position where the image is focused on the CCD surface is shifted by moving the lens system of CCD area sensors in advance so that contrast differences between display operating portions and display non-operating portions of the display device will not occur. Hereinafter, the state in which the image is focused on the CCD surface is referred to as a "focused state," and the state in which the image cannot be focused is referred to as a "defocused state."

Figure 10A:
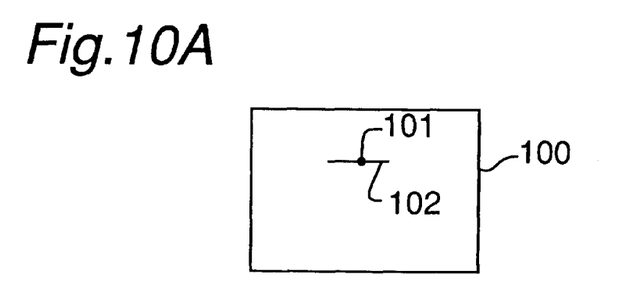
FIG. 10A is a view showing a display pixel.
Figure 10B:
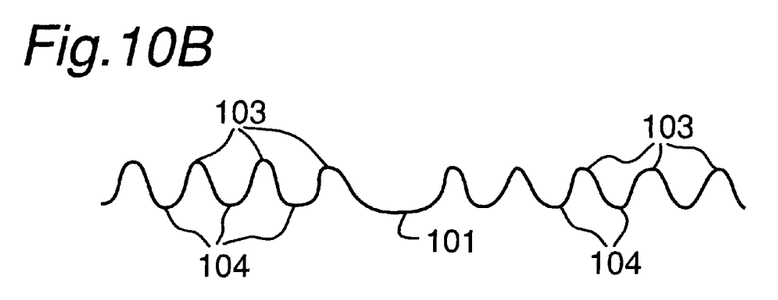
FIGS. 10B and 10C are views showing density data distributions in the focused state and in the defocused state, respectively.
Figure 10C:
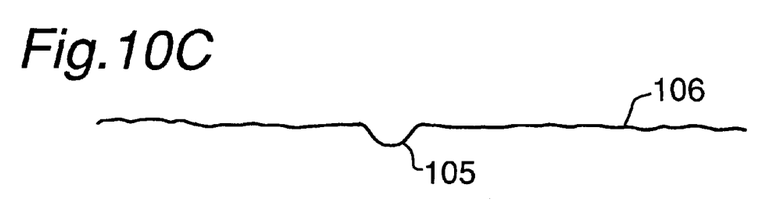

Now consider a display pixel 100 as shown in FIG. 10A. Assume that a dark-dot defect 101, as shown in FIG. 10A, is present on this display pixel 100. FIG. 10B shows density distribution data in the focused state at ten display operating portions on a one-dimensional reference line 102 on the display pixel 100, where display operating portions 103 and display non-operating portions 104 are part of them. Also, the dark-dot defect 101 is present in this density distribution data. FIG. 10C shows density distribution data in the defocused state of the display pixel 100, where a dark-dot defect portion 105 (a defocused state of the dark-dot defect 101) is present in a background density 106. This background density 106 is a defocused state part of the display operating portion 103 and the display non-operating portion 104.

This conventional method is frequently used for large degrees of point defects, being an effective method. A contrast difference between display operating portions and display non-operating portions in this case refers to a contrast difference in the sensor pixel that has received light.

However, the aforementioned conventional method raises the following issues.

Making a defocused state, as described above, would result in reduced contrast differences between point-defect portions and normal portions, such that the method could not maintain enough detection ability for small degrees of point defects. In other words, making a defocused state until the difference between the display operating portions and the display non-operating portions of the display device is nullified would cause the contrast differences of small degrees of point defects to be eliminated. Thus, the conventional method has a disadvantage of being incapable of detecting such small degrees of point defects.

In some cases, it is necessary to decide whether or not the position of a display operating portion of the display device is normal. However, as described above, making a defocused state would make it difficult to decide where the proper position of the display operating portion should be.

In other cases, it is necessary to decide whether or not the size of a display operating portion of the display device is normal. However, as described above, making a defocused state would make it difficult to decide how the proper size of the display operating portion should be.

SUMMARY OF THE INVENTION

The object of the present invention, in order to solve the above-discussed issues, is to provide a display screen inspection method which eliminates the need of making a defocused state and which is capable of inspecting a display screen for its operating portions at a high speed without requiring any complex processing algorithms.

In accomplishing these and other aspects, according to a first aspect of the present invention, there is provided a display screen inspection method for taking a display screen of a display device as an inspection subject and making decisions on defects of the display screen, the method comprising:

performing a separation between display operating portions and display non-operating portions of the inspection subject present in a gray image from image data of individual pixels of the gray image obtained by picking up an image of the inspection subject;

selectively extracting image data of only proper display operating portions and compressing the image data to be inspected for defects; and inspecting the selectively extracted image data for any defects.

According to a second aspect of the present invention, there is provided a display screen inspection method according to the first aspect, wherein in the selectively extracting, a position of each of the display operating portions is given by a pixel showing a peak of density data out of the density data of the gray image, a resulted value of a calculation with the density data of the peak and density data of pixels around the peak is taken as representative density data of the display operating portion, and image data of only the proper display operating portions are selectively extracted based on both the positions of the display operating portions and the representative density data.

According to a third aspect of the present invention, there is provided a display screen inspection method according to the second aspect, wherein in the selectively extracting, for obtaining the position of the display operating portion and the representative density data, even if no peak of the density data is present, density data of a position where a display operating portion should be present is selectively extracted from density data of display operating portions before and after the position.

According to a fourth aspect of the present invention, there is provided a display screen inspection method according to any of the first to third aspects, wherein in the selectively extracting, a position of each of the display operating portions is given by a pixel showing a peak of density data out of density data of the gray image, and a resulting value of a calculation with the density data of the peak and density data of pixels around the peak is taken as representative density data of the display operating portion, and wherein in the inspecting, any shift of a peak portion is detected by detecting a portion having different positional data intervals of display operating portions before and after the peak from positional data of the peak of the density data.

According to a fifth aspect of the present invention, there is provided a display screen inspection method according to any of the first to fourth aspects, wherein in the selectively extracting, a position of each of the display operating portions is given by a pixel showing a peak of density data out of density data of the gray image, a resulting value of a calculation with the density data of the peak and density data of pixels around the peak is taken as representative density data of the display operating portion, and wherein in the inspecting, it is decided whether or not any defect in size of an area of the display operating portion is present by counting a number of density data that exceed a reference density calculated from the representative density data out of the density data of the pixels around the peak.

With the above constitution of the present invention, the following functional effects can be produced.

In the separation process, display operating portions and display non-operating portions of the inspection subject present in the gray image are separated from each other on the basis of density data of individual pixels of the gray image obtained by picking up an image of the inspection subject. In the selective extraction process, image data of only the proper display operating portions where they should be operated are selectively extracted and image data to be inspected for defects are compressed. Further, in the inspection process, the selectively extracted image data is subjected to the defect inspection process. Thus, the inspection in the focused state is enabled without the need of making a defocused state, so that light can be received by image pickup devices, e.g. sensor pixels, without losing density data of small degrees of point defects.

Furthermore, it is conventionally the case that the space of the image processing memory is allocated to display operating portions and display non-operating portions in performing the display screen inspection process, and that the processing would be carried out for the density data of the entire space. However, in the case of the display screen inspection method of the present invention, because only the density data of display operating portions corresponding to the display pixels of the display device are selectively extracted, the amount of density data to be treated in the actual inspection process can be significantly reduced to an extremely small amount. As a result of this, of course, a great effect for reducing the processing time can be obtained.

Also, the present invention is able to decide whether or not the position of a display operating portion of the display device is normal, or whether or not the size of a display operating portion of the display device is normal.

BRIEF DESCRIPTION OF THE DRAWINGS

These and other aspects and features of the present invention will become clear from the following description taken in conjunction with the preferred embodiments thereof with reference to the accompanying drawings, in which.

DETAILED DESCRIPTION OF THE PREFERRED EMBODIMENTS

Before the description of the present invention proceeds, it is to be noted that like parts are designated by like reference numerals throughout the accompanying drawings.

Hereinbelow, embodiments of the present invention are described with reference to the accompanying drawings.

In a display screen inspection method according to a first embodiment of the present invention, a liquid crystal display (LCD) is used as an example of the display device, and CCD area sensors are used as an example of the image pickup devices.

The display device, the CCD area sensors, and an image memory have an expanse of perpendicular two dimensions. However, explaining with a two-dimensional expanse would result in a complexity in vain, hindering the understanding, and besides an understanding with either one dimension of the two dimensions can easily be extended to an understanding of two dimensions. Therefore, the explanation here is made with one dimension. Also, because the display device and the CCD area sensors are both fabricated by photolithography of high dimensional precision, the pitch of the display pixels and the pitch of the sensor pixels of the CCD area sensors are so assumed that their design data will be maintained even with changed subjects. In this connection, it is also assumed that influences of partial distortions, blurs, or the like due to the optical system are neglected.

Herein, the intensity of light emitted by the display device is referred to as "light intensity." The light intensity being expressed in any arbitrary unit, the intensity of light per unit area emitted by the individual pixels of the display device, the intensity of light integrated over the entire range of the display pixels, and the intensity of light per unit area of the pixel image formed on the photoreceptive surfaces of the sensor pixels are all expressed also as "light intensity."

Figure 1:
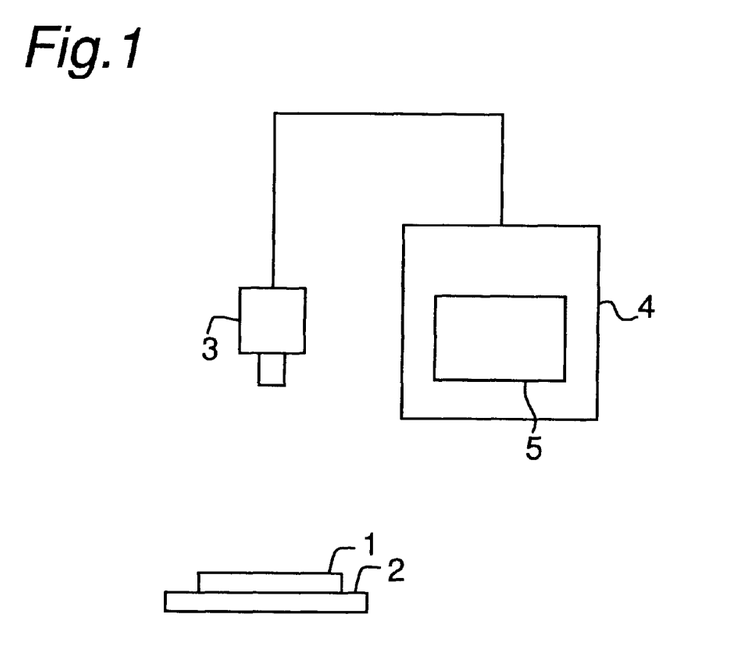
FIG. 1 is a schematic diagram of a display screen inspection apparatus for embodying a display screen inspection method used in a first embodiment of the present invention.

FIG. 1 is a schematic diagram of a display screen inspection apparatus according to the first embodiment of the present invention. A display device 1, which is the inspection subject, is set on an inspection stage 2 where alignment marks of the display device 1 are detected by a known method so that a correct alignment between the display device 1 and the inspection stage 2 is achieved. By this alignment process, the positional relation between an inspection camera 3, having image pickup devices, and the display device 1 is maintained generally constant. In particular, any two-dimensional rotational shifts are resolved at all times by this alignment. In addition, even with any rotational shifts, the rotational angle of the inspection subject can be properly adjusted through an image rotating process by determining the positions of surrounding display portions (display pixels on the surroundings) of the inspection subject.

Image data from the sensor pixels of the image pickup devices in the inspection camera 3 are associated with the sensor pixels in a one-to-one correspondence, and are transferred to the image memory 5 in a computer 4. Needless to say, within the computer 4 are stored programs for reading the image data of the image memory 5 and for performing specified defect processing. For example, in a typical inspection of point defect processing, stored as the programs in the computer 4 is an image processing algorithm in which a comparison between image data of points to be inspected and image data around the point is made, wherein if a pixel having an extremely smaller density level of image data than those around the pixel is present, the pixel is decided as a dark dot, while if a pixel having an extremely larger density level of image data than those around the pixel is present, the pixel is decided as a bright dot. Also, in the inspection of linear defect processing, any portion where bright dots or dark dots are continued in the direction of either row or column is decided as a bright line or a dark line.

Figure 2:
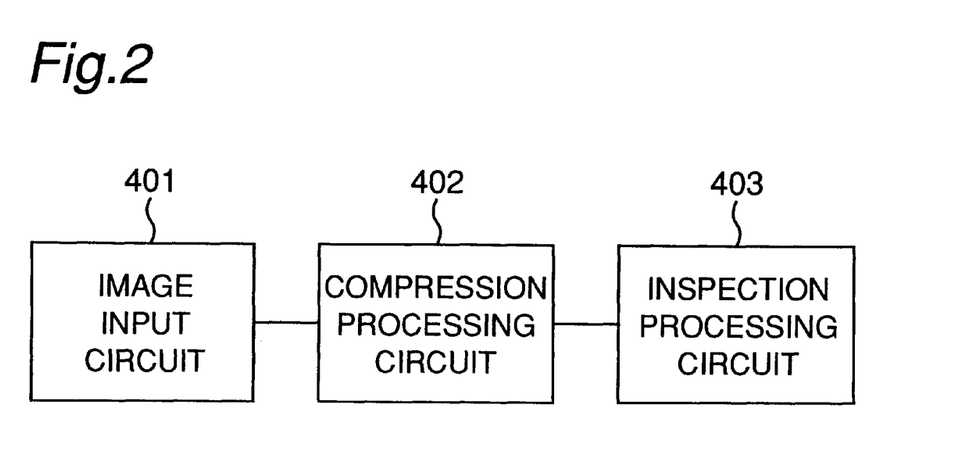
FIG. 2 is a processing circuit block diagram of the apparatus used in the first embodiment of the present invention.

FIG. 2 shows a processing circuit block diagram for implementing the above embodiment of the present invention. This processing circuit is built in the computer 4 of the apparatus of FIG. 1. First, image data derived from the inspection camera 3 which is an image pickup device, is stored into the computer 4 by an image input circuit 401. Next, only necessary image data out of the stored image data is extracted by a compression processing circuit 402 which is described below, and is subjected to a compressing process. Finally, the compressed image data are processed with the programs previously stored in the computer 4 to activate the image processing algorithm with an inspection processing circuit 403.

Figure 3A:
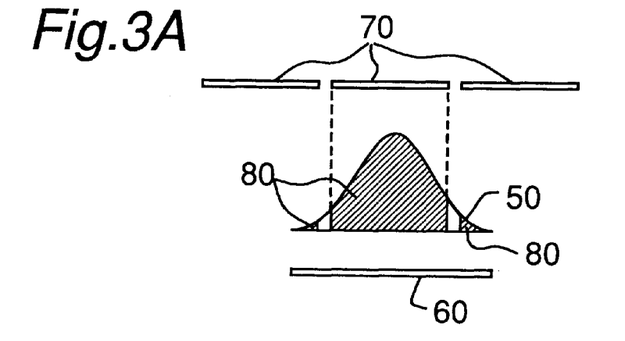
FIGS. 3A and 3B are views showing the relative positional relation between display pixels and sensor pixels.
Figure 3B:
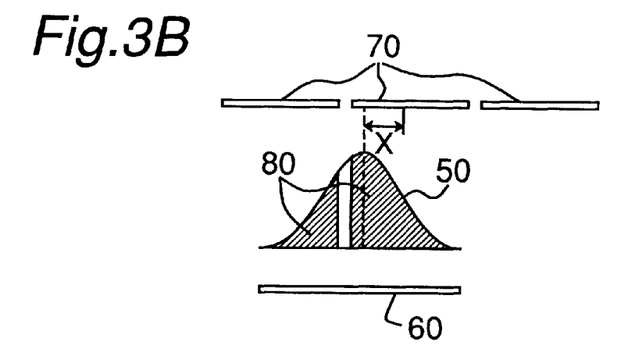

FIGS. 3A and 3B show a light intensity distribution 50 of a display pixel image in its positional relation with a display pixel image area 60. In the figure, there is also shown a sensor-pixel area 70 in its positional relation with the light intensity distribution 50 and the display pixel image area 60. In this case, two examples are shown in FIGS. 3A and 3B. That is, FIG. 3A illustrates a case where the center of the sensor-pixel area 70 is at the peak position of the light intensity distribution 50, while FIG. 3B illustrates a case where the center of the sensor-pixel area 70 is X distance away from the peak position of the light intensity distribution 50. The intensity of light received by a sensor pixel is a value resulting from integrating the light intensity over the effective area of the sensor pixel, hence a quantity expressed by the shaded portions 80 in the figure. The light intensity distribution of a display device generally tends to have a peak in a central portion of a display pixel, and to decrease in light intensity toward the end portions thereof. Naturally, the closer the center of the display pixel and the center of the sensor pixel are to each other, the greater the intensity of light received by the sensor pixel becomes. In the example of FIGS. 3A and 3B, the maximum number of sensor pixels affected by the display pixel image area 60 is three. That is, the light intensity of the display pixel image area 60 can be determined by integrating the light intensities of pertinent sensor pixels. In this embodiment, the maximum number of allocated sensor pixels relative to the display pixels is determined beforehand.

Figure 4:
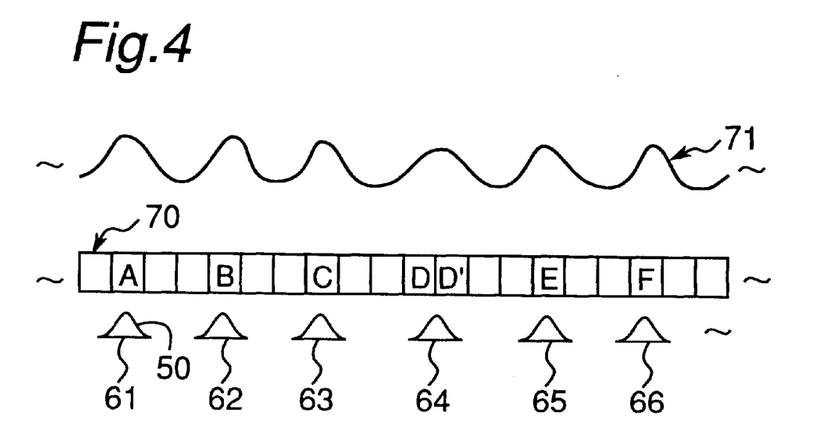
FIG. 4 is a view showing one-dimensional density data of sensor pixels.

FIG. 4 shows density data 71 on the image memory obtained from twenty sensor pixels 70 that are extended one-dimensionally. Largenesses and smallnesses of the density data are iteratively strung from the density data 71 by the compression processing circuit 402, as shown in FIG. 10B, by which the decision as to portions where display pixels are present and portions where no display pixels are present is made. From the optical magnification, a reference sensor-pixel interval $P_{std}$ at the peak portion is determined. In FIG. 4, it is about 3.3 pixels. When the inspection subject has no defects, peak portions are repeated according to the reference sensor-pixel interval $P_{std}$. In order to detect the density data of portions where no peak portion is present but a peak portion should be present, the following criteria are given, where if the criteria are not satisfied, a compression transform process is performed. Assume that these criteria are a reference interval lower-limit ratio D and a reference interval upper-limit ratio U. Approximate values 0.5 for D and 1.5 for U are used in the actual processing, empirically.

From this setting, the reference interval lower-limit threshold $D_{thr}$ and the reference interval upper-limit threshold $U_{thr}$ become as follows, where the following decisions are made depending on P, which is the determined interval between peak portions:

$$D_{thr}=P_{std}\times D$$
$$U_{thr}=P_{std}\times U \quad (1)$$

1) if $P<D_{thr}$, then portions of small density data out of peak portions associated with P are excluded from the peak portions; and 2) if $P>U_{thr}$, then density data located at positions in compliance with $P_{std}$ are extracted to the number of $(P/P_{std})$ in the interval P.

Figure 6:
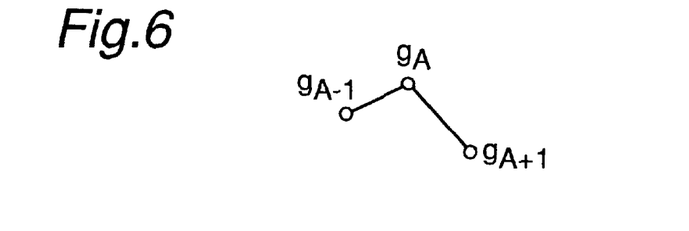
FIG. 6 is a view showing a density distribution before and after a sensor pixel having a peak density.

In the case of FIG. 4, it is determined from these equations that $D_{thr}$ is about 1.7 pixels and $U_{thr}$ is about 5.0 pixels. The case 1) is directed to a compression-transform processing method for extremely small intervals of peak portions, and the case 2) is directed to a compression-transform processing method for extremely large intervals of peak portions. From the density data 71, peak portions A, B, C, D (=D'), E, and F are detected in this order. In this case, the intervals of the peak portions A, B, C, D (=D'), E, and F satisfy the conditions of $D_{thr}$ and $U_{thr}$. As confirmed beforehand, the maximum number of sensor pixels that are affected by the display pixel image area 60 is three, and therefore, representative density data with respect to display pixels 61 to 66 is given by an average density value of three pixels consisting of peak density data and the two pixels before and after the peak density data. Also, although the pixel position of the peak portion may be taken as the position of the peak portion as it is without any problem, the position of the peak portion is further correctly determined as follows. As shown in FIG. 6, taking a peak portion A as an example, density data of the peak portion A and portions before and after the peak portion A are assumed as $g_{A-1}$, $g_A$, $g_{A+1}$, and the positions of sensor pixels corresponding to these are assumed as $P_{A-1}$, $P_A$, and $P_{A1}$. Then, the position of the display pixel can be determined from a weighted mean of these three pixels as follows:

$$(g_{A-l} \times p_{A-l} + g_A + g_{A+l} \times p_{A+l})/(g_{A-l} + g_{A-l}) \quad (2)$$

where when the same density data as that of the adjacent portion is involved like D, it is decided beforehand which is adopted out of the first and second. Here, twenty sensor pixels that have been counted are compression transformed into six pieces of representative density data of display pixels as shown in FIG. 4.

There are some cases where a peak portion is not present at a predetermined position. These are cases in which the aforementioned interval P of peak portions exceed $U_{thr}$. For example, if a peak portion should be present at an interval of 3 or 4 pixels and if a peak portion is not present at an interval about 1.5 times larger than the interval, the average value of density data of three pixels at and around a position where a peak portion should be present is forcedly stored at the position as representative density data.

Figure 5:
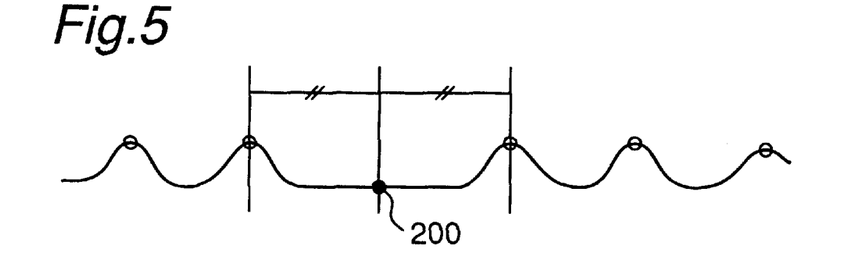
FIG. 5 is a view showing one-dimensional density data of a sensor pixel with no one peak present.

FIG. 5 shows an example in which one peak portion is absent at the position where it should be present, and the one peak portion is compensated based on two peak portions before and after the one peak portion. In addition, the portion marked "●" is a pixel 200 where the peak portion should be present.

Finally, the image algorithm of defect processing is applied to the compression-transformed image by the inspection processing circuit 403. Consequently, in the typical point-defect processing inspection, a comparison between image density data of a pixel and image density data of pixels around the pixel is made, where a pixel of extremely smaller image data than each of those of pixels around the pixel, if present, are decided as dark dots, while a pixel of extremely larger image density data than each of those of pixels around the pixel, if present, are decided as bright dots.

Next, a display screen inspection method according to a second embodiment of the present invention is described with reference to FIG. 7. In this case, the present invention is enabled to detect any shift of peak portions by referencing a determined position of a display pixel on the sensor pixel.

Figure 7:
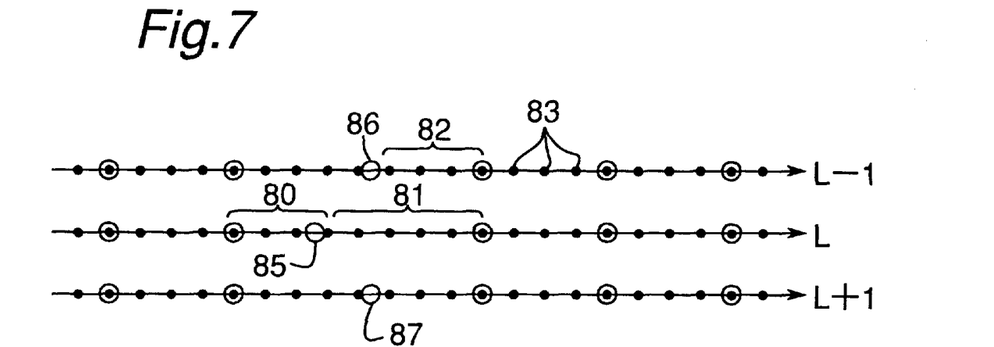
FIG. 7 is a view showing pixel intervals of display pixels that the sensor pixels have captured for explaining a display screen inspection method according to a second embodiment of the present invention.

FIG. 7 shows display pixel arrays, L−1, L, and L+1, where display operating portions are present. A portion marked "○" is the display pixel center, which is the peak portion of density data determined by the above calculation. Sensor pixels are present at portions marked "•", such as 83, with equal intervals. If the reference sensor-pixel interval $P_{std}$, is about 4 pixels, as shown in the figure, it is confirmed in FIG. 7 that given a normal peak-portion interval of 82, abnormal intervals are present at 80 and 81. The detection of these abnormal intervals is achieved also by comparing the positions of peak portions above and below a target peak portion. With respect to a peak portion 85, which is an abnormal position, display pixel arrays L−1, L, and L+1 above and below the peak portion 85 are confirmed and then positional differences of the display pixel arrays L−1, L, and L+1 from the positions of peak portions 86 and 87 are determined. If each of these differences is in excess of a specified threshold interval, the target peak portion is decided to be a portion that causes an abnormal interval to take place.

Next, a display screen inspection method according to a third embodiment of the present invention is described with reference to FIG. 8. In this case, the present invention is enabled to evaluate the size of display pixels.

Figure 8:
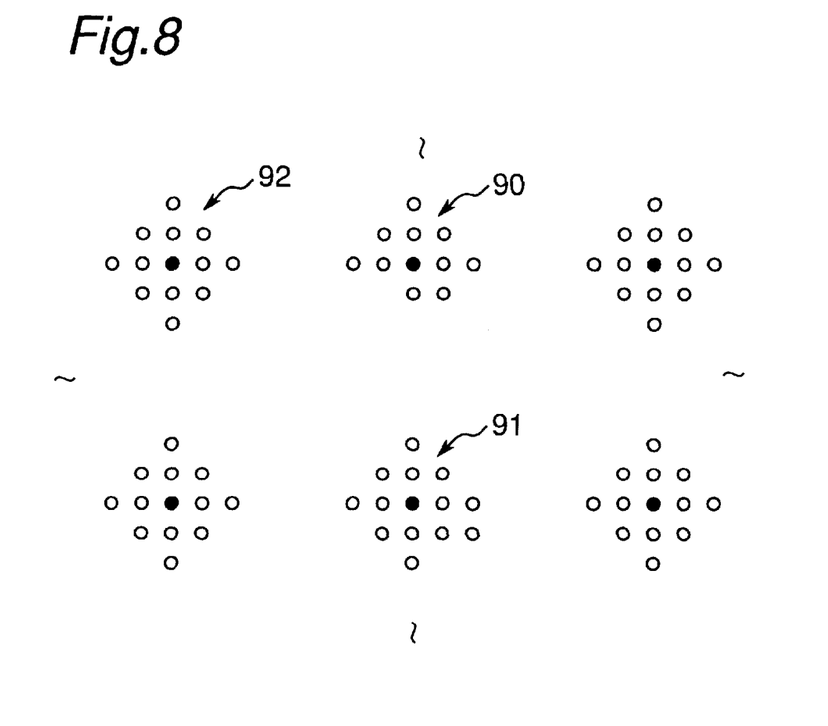
FIG. 8 is a view showing sensor pixels allocated to two-dimensionally spread display pixels for explaining a display screen inspection method according to a third embodiment of the present invention.

FIG. 8 shows part of display pixels that have been expanded two-dimensionally. The mark "○" represents a sensor pixel regarded as a display operating portion, and the mark "●" represents a sensor pixel having peak density data among the display operating portions. In this case, thirteen sensor pixels are allocated to a display pixel in a standard fashion. Judging from experience, when ten or more sensor pixels are allocated to a display pixel in a standard fashion, counting the sensor pixels that have density data higher than a certain ratio and that are present around peak density data makes it possible to decide the size of the display pixel. Performing the inspection of point defect processing with respect to a compression-transformed image and evaluating the number of sensor pixels recognized as the display operating portions enhances the performance of defect processing. In FIG. 8, for example, it is assumed that if the number of sensor pixels is eleven or less, then the size of the display pixel is too small, and if the number of sensor pixels is fifteen or more, then the size of the display pixel is too large, and if the number of sensor pixels is twelve through fourteen, then the size of the display pixel is normal. Then, in FIG. 8, numeral 90 indicates that the number of sensor pixels is as small as eleven, and 91 indicates that the number of sensor pixels is as large as fifteen. Numeral 92 denotes a standard portion of thirteen sensor pixels.

In the display screen inspection methods according to the first to third embodiments of the present invention, since pixel data of only display operating portions of the display screen are extracted, there can be produced a compression effect of image data of necessary portions only.

Figure 9:
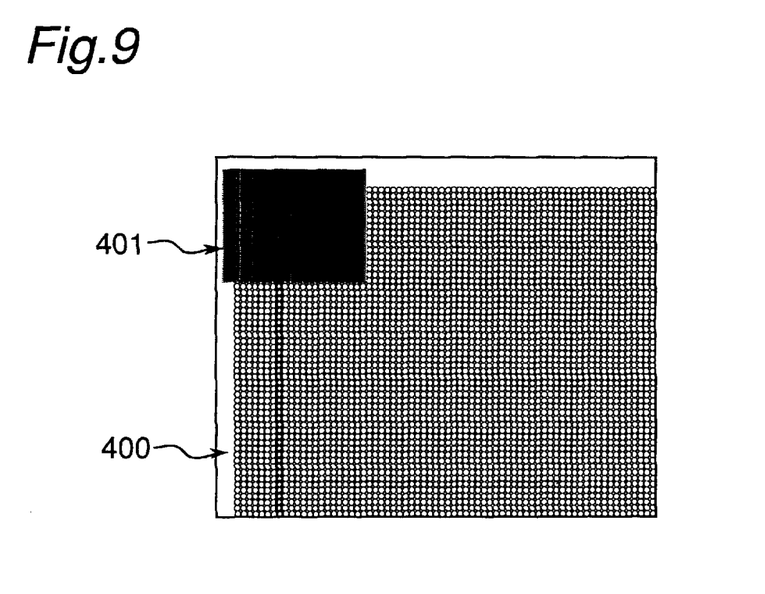
FIG. 9 is a view showing images before and after compression as they are stacked one on another.

For example, when three sensor pixels are allocated to one pixel pitch of display pixels in the horizontal direction of the display screen, the compression effect in the horizontal direction is ⅓. Likewise, when a compression effect of ⅓ is also obtained in the vertical direction, a compression effect of ⅑ as a whole can be obtained. FIG. 9 is an example in which an uncompressed image 400 of an inspection subject including bright-line defects and a compressed image thereof (see an image 401 of a small square at the upper left) are displayed in superimposition, in an application of one embodiment of the present invention. A compression of about ⅓ has been effected in both horizontal and vertical directions.

For instance, when a captured image has an image memory space of 2000×2000, then the ⅑ compressed image becomes an image memory space of about 660×660. It is needless to say that since the processing time differs depending on the amount of process data, a large effect is produced for the reduction in processing time. Further, the separating of display operating portions and display non-operating portions of the display pixels from each other makes it possible to capture subtle changes in brightness. Conventionally, since the evaluation of brightness has been implemented in a state such that display operating portions and display non-operating portions are mixed together, the display operating portions would be affected by the display non-operating portions such that it has been impossible to capture subtle changes in brightness.

With the second embodiment of the present invention, the present invention is enabled to extract positional intervals of display operating portions of the display device, so that the operating at any abnormal positions can be confirmed. For example, let us take a case of a color liquid crystal panel. In the color liquid crystal panel, there are formed red, green, and blue in order and with regularity on the color filter. In normal liquid crystal panels, for the operating of the red color, light is transmitted only by the liquid crystal elements of red color portions. However, in a liquid crystal panel in which defects are present, there occur some cases where a red color that should light up does not but its adjacent green color lights up in the red color. For the present invention, it is possible to judge such defects by evaluating the positional intervals of display operating portions.

In some CRT panels, there is a defect that the size of display operating portions is varied. This is referred to as large holes or small holes. With the third embodiment of the present invention, it is possible to judge such defects by evaluating the size of display operating portions.

Accordingly, the present invention is a general-purpose method that can be widely applied to the inspections of display screens of various types of display devices.

The entire disclosure of Japanese Patent Application No. 8-169782filed on Jun. 28, 1996, including the specification, claims, drawings, and summary, are incorporated herein by reference in its entirety.

Although the present invention has been fully described in connection with the preferred embodiments thereof with reference to the accompanying drawings, it is to be noted that various changes and modifications are apparent to those skilled in the art. Such changes and modifications are to be understood as being included within the scope of the present invention as defined by the appended claims unless they depart therefrom.

What is claimed is:

1. A display screen inspection method for taking a display screen of a display device as an inspection subject and making decisions on defects of the display screen, said method comprising:

performing a separation between display operating portions and display non-operating portions of the inspection subject present in a gray image from image data of individual pixels of the gray image obtained by picking up an image of the inspection subject;

selectively extracting image data of only proper display operating portions and compressing the image data to be inspected for defects; and inspecting the selectively extracted image data for any defects;

wherein in said selectively extracting, a position of each of the display operating portions is given by a pixel showing a peak of density data out of the density date of the gray image, a resulting value of a calculation with the density data of the peak and density data of pixels around the peak is taken as representative density data of the display operating portion, and image data of only the proper display operating portions are selectively extracted based on both the positions of the display operating portions and the representative density data.

2. A display screen inspection method as claimed in claim 1, wherein in said selectively extracting for obtaining the position of the display operating portion and the representative density data, even if no peak of the density data is present, density data of a position where a display operating portion should be present is selectively extracted from density data of display operating portions before and after the position.

3. A display screen inspection method as claimed in claim 2, wherein in said selectively extracting, a position of each of the display operating portions is given by a pixel showing a peak of density data out of the density data of the gray image, and a resulting value of a calculation with the density data of the peak and density data of pixels around the peak is taken as representative density data of the display operating portion; and wherein in said inspecting, any shift of a peak portion is detected by detecting a portion having different positional data intervals of display operating portions before and after the peak from positional data of the peak of the density data.

4. A display screen inspection method as claimed in claim 2, wherein in said selectively extracting, a position of each of the display operating portions is given by a pixel showing a peak of density data out of the density data of the gray image, and a resulting value of a calculation with the density data of the peak and density data of pixels around the peak is taken as representative density data of the display operating portion; and wherein in said inspecting, it is decided whether or not any defect in size of an area of the display operating portion is present by counting a number of density data that exceed a reference density calculated from the representative density data out of the density data of the pixels around the peak.

5. A display screen inspection method as claimed in claim 1, wherein in said selectively extracting, a position of each of the display operating portions is given by a pixel showing a peak of density data out of the density data of the gray image, and a resulting value of a calculation with the density data of the peak and density data of pixels around the peak is taken as representative density data of the display operating portion; and wherein in said inspecting, any shift of a peak portion is detected by detecting a portion having different positional data intervals of display operating portions before and after the peak from positional data of the peak of the density data.

6. A display screen inspection method as claimed in claim 1, wherein in said selectively extracting, a position of each of the display operating portions is given by a pixel showing a peak of density data out of the density data of the gray image, and a resulting value of a calculation with the density data of the peak and density data of pixels around the peak is taken as representative density data of the display operating portion; and wherein in said inspecting, it is decided whether or not any defect in size of an area of the display operating portion is present by counting a number of density data that exceed a reference density calculated from the representative density data out of the density data of the pixels around the peak.

7. A display screen inspection method for taking a display screen of a display device as an inspection subject and making decisions on defects of the display screen, said method comprising:

performing a separation between display operating portions and display non-operating portions of the inspection subject present in a gray image from image data of individual pixels of the gray image obtained by picking up an image of the inspection subject;

selectively extracting image data of only proper display operating portions and compressing the image data to be inspected for defects; and inspecting the selectively extracted image data for any defects;

wherein in said selectively extracting, a position of each of the display operating portions is given by a pixel showing a peak of density data out of the density data of the gray image, and a resulting value of a calculation with the density data of the peak and density data of pixels around the peak is taken as representative density data of the display operating portion; and wherein in said inspecting, any shift of a peak portion is detected by detecting a portion having different positional data intervals of display operating portions before and after the peak from positional data of the peak of the density data.

8. A display screen inspection method as claimed in claim 7, wherein in said selectively extracting, a position of each of the display operating portions is given by a pixel showing a peak of density data out of the density data of the gray image, and a resulting value of a calculation with the density data of the peak and density data of pixels around the peak is taken as representative density data of the display operating portion; and wherein in said inspecting, it is decided whether or not any defect in size of an area of the display operating portion is present by counting a number of density data that exceed a reference density calculated from the representative density data out of the density data of the pixels around the peak.

9. A display screen inspection method for taking a display screen of a display device as an inspection subject and making decisions on defects of the display screen, said method comprising:

performing a separation between display operating portions and display non-operating portions of the inspection subject present in a gray image from image data of individual pixels of the gray image obtained by picking up an image of the inspection subject;

selectively extracting image data of only proper display operating portions and compressing the image data to be inspected for defects; and inspecting the selectively extracted image data for any defects;

wherein in said selectively extracting, a position of each of the display operating portions is given by a pixel showing a peak of density data out of the density data of the gray image, and a resulting value of a calculation with the density data of the peak and density data of pixels around the peak is taken as representative density data of the display operating portion; and wherein in said inspecting, it is decided whether or not any defect in size of an area of the display operating portion is present by counting a number of density data that exceed a reference density calculated from the representative density data out of the density data of the pixels around the peak.

* * * * *